United States Patent
Hausotte

(10) Patent No.: US 9,478,027 B2
(45) Date of Patent: Oct. 25, 2016

(54) METHOD FOR EVALUATING AN EXAMINATION

(71) Applicant: Siemens Aktiengesellschaft, Munich (DE)

(72) Inventor: Annemarie Hausotte, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/481,995

(22) Filed: Sep. 10, 2014

(65) Prior Publication Data

US 2015/0078639 A1    Mar. 19, 2015

(30) Foreign Application Priority Data

Sep. 19, 2013  (DE) .................. 10 2013 218 806

(51) Int. Cl.
*G06T 7/00*    (2006.01)
*G06F 19/00*    (2011.01)

(52) U.S. Cl.
CPC .......... *G06T 7/0014* (2013.01); *G06F 19/321* (2013.01); *G06T 7/0081* (2013.01); *G06T 7/0097* (2013.01); *G06T 2207/20112* (2013.01); *G06T 2207/30004* (2013.01)

(58) Field of Classification Search
None
See application file for complete search history.

(56) References Cited

U.S. PATENT DOCUMENTS

| | | | | |
|---|---|---|---|---|
| 2008/0004520 A1* | 1/2008 | Theriault | ............... | A61B 5/055 600/410 |
| 2009/0324031 A1* | 12/2009 | Gee | ........................ | G06T 7/0024 382/128 |
| 2011/0036360 A1* | 2/2011 | Lang | ..................... | A61B 6/505 128/898 |

FOREIGN PATENT DOCUMENTS

WO    WO-2007147059 A2    12/2007

* cited by examiner

*Primary Examiner* — Siamak Harandi
*Assistant Examiner* — Amandeep Saini
(74) *Attorney, Agent, or Firm* — Harness, Dickey & Pierce

(57) ABSTRACT

A method is disclosed for evaluating an examination of an examination object using a medical imaging device by way of an evaluation unit. The method includes reading in an examination data set of the examination object; assigning a reference data set to the read-in examination data set, the reference data set comprising at least one reference region; selecting at least one reference region; assigning at least one examination region of the examination data set to the at least one reference region; and marking the at least one examination region in at least one image of the examination data set. In an advantageous embodiment, the marking of the at least one examination region includes a marking tolerance and a segmentation of the at least one examination region on at least one image of the examination data set, and the segmentation depends on the medical imaging device.

9 Claims, 3 Drawing Sheets

METHOD FOR EVALUATING AN EXAMINATION

PRIORITY STATEMENT

The present application hereby claims priority under 35 U.S.C. §119 to German patent application number DE 102013 218806.4 filed Sep. 19, 2013, the entire contents of which are hereby incorporated herein by reference.

FIELD

At least one embodiment of the present invention generally relates to a method for evaluating an examination of an examination object using a medical imaging device, a corresponding evaluation unit, a medical evaluation system, a computer program which enables the execution of such a method and/or a computer-readable storage medium.

BACKGROUND

The evaluation of medical image data is a common task, particularly in clinical application.

In everyday clinical practice suitable preprocessing of medical image data, in particular for an efficient and targeted evaluation or diagnosis, may represent an extremely complex problem, especially if a large amount of medical image data is available.

SUMMARY

At least one embodiment of the invention is to specify a method which facilitates an evaluation of such image data and with which it is possible in a simple manner to output a relevant examination region determined by way of the image data, as a function of different parameters.

A method, an evaluation unit, a medical evaluation system, a computer program, and a computer-readable storage medium are disclosed. Advantageous embodiments of the invention are specified in the respective related subclaims.

In connection with an embodiment of the present invention an evaluation unit for evaluating an examination of an examination object using a medical imaging device is also provided.

In an embodiment, a method for evaluating an examination of an examination object using a medical imaging device by means of an evaluation unit is provided, comprises:

Reading in an examination data set of the examination object,

Assigning a reference data set to the read-in examination data set, the reference data set comprising at least one reference region, Selecting at least one reference region, Assigning at least one examination region of the examination data set to the at least one reference region and Marking the at least one examination region in at least one image of the examination data set.

The evaluation unit of an embodiment comprises a processing unit and is configured to perform at least the following:

Reading in an examination data set of the examination object by means of the processing unit, Assigning a reference data set to the read-in examination data set by means of the processing unit, the reference data set comprising at least one reference region, Selecting at least one reference region by means of the processing unit, Assigning at least one examination region of the examination data set to the at least one reference region by means of the processing unit and Marking the at least one examination region in at least one image of the examination data set by means of the processing unit.

Furthermore, a medical evaluation system, comprising an evaluation unit and at least one medical imaging device, is provided for evaluating an examination of an examination object.

Further, an embodiment of the present invention describes a computer program which can be loaded in a memory unit of a programmable controller or a computing unit of an evaluation unit and/or of a medical evaluation system. With this computer program, all or various previously described embodiments of the inventive method can be executed, if the computer program runs in the controller or control facility of the evaluation unit and/or of the medical evaluation system. In such cases the computer program requires possible program means, e.g. libraries and auxiliary functions, in order to realize the corresponding embodiments of the method. In other words, software with which one of the above-described embodiments of the inventive method can be executed or which executes this embodiment is in particular to be protected with the claim focusing on the computer program. In such cases, the software may be a source code, which must still be compiled and bound or which only has to be interpreted, or an executable software code, which is to be loaded for execution purposes into the corresponding computing unit.

Furthermore, an embodiment of the present invention relates to an electronically readable storage medium, e.g. a DVD, a magnetic tape or a USB stick, on which electronically readable control information, in particular software, is stored. If this control information is read from the storage medium and stored in a controller or computing unit of an evaluation unit and/or of a medical evaluation system, all inventive embodiments of the previously described method can be implemented.

BRIEF DESCRIPTION OF THE DRAWINGS

The invention is described and explained in more detail below with reference to the exemplary embodiments illustrated in the figures, in which.

DETAILED DESCRIPTION OF THE EXAMPLE EMBODIMENTS

Figure 1:
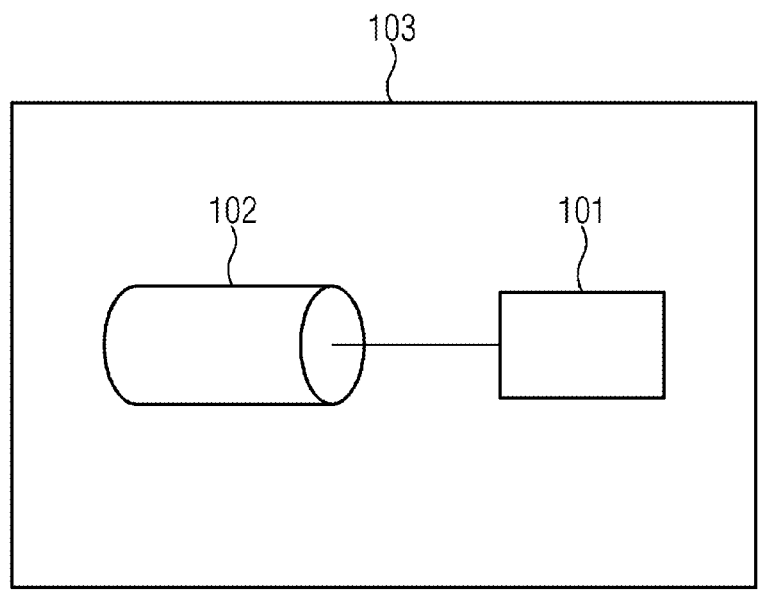
FIG. 1 shows an embodiment of an inventive medical evaluation system.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing"

or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In an embodiment, a method for evaluating an examination of an examination object using a medical imaging device by means of an evaluation unit is provided, comprises:

Reading in an examination data set of the examination object,
Assigning a reference data set to the read-in examination data set, the reference data set comprising at least one reference region,
Selecting at least one reference region,
Assigning at least one examination region of the examination data set to the at least one reference region and
Marking the at least one examination region in at least one image of the examination data set.

A medical imaging device is a device, preferably an electronic and/or IT device, for capturing, processing, evaluating and/or storing image information in the form of image data. To capture the image information, it is possible for example to use acoustic methods such as ultrasound (US), emission methods such as emission computed tomography (ECT) and positron emission tomography (PET), optical methods, and radiological methods such as X-ray tomography and computed tomography (CT), but the capture can also take place using magnetic resonance tomography (MR or MRT) or using combined methods. The medical imaging device may supply 2-dimensional (2D) or multidimensional image data, for instance 3-dimensional (3D) or 4-dimensional (4D), which can preferably be stored and/or processed in different formats. The medical imaging device can be used in diagnostics, for example in medical diagnostics.

Reading in an examination data set of the examination object comprises reading in at least one image of the examination object. When reading in more than one image it is also possible for the images to originate from different modalities, in other words different medical imaging devices. The examination object preferably comprises a patient.

Assigning a reference data set to the read-in examination data set comprises assigning data from a so-called standard patient to the examination object. In this case the standard patient is generally not the current examination object to be examined. Instead, the standard patient comprises information from a plurality of patients who are similar to the examination object in a predefined manner. The similarity to the examination object may be established for example by age, sex, size, preexisting or underling diseases or other features defined by a medical specialist. The standard patient may for example be represented by an average image of this plurality of patients. The inventive solution preferably comprises holding several standard patients available, so that a representative standard patient can be assigned for a plurality of examination objects.

The reference data set for the standard patient further comprises at least one reference region, i.e. a particularly outstanding examination region which is advantageous for the evaluation of the examination. In this case a position of the reference region, in particular a location and/or an extent of the reference region within the standard patient, is to be regarded as known.

The at least one reference region of the reference data set is for example selected manually by a user or else by means of a manual or automatic selection of one or more reference regions from a predefined list of reference regions. Criteria for such a selection may take account of a region specifically to be examined of the examination object or of other parameters. This facilitates identification of a particular examination region and thus a subsequent image evaluation.

Then at least one examination region of the examination data set is assigned to the at least one selected reference region.

At least one embodiment of the invention uses the marking of the at least one examination region on at least one image of the examination data set in addition to the actual establishment of the position, in particular the location and/or extent, of an examination region within the examination object. In this case marking for example means selecting a data matrix from the examination data set or else visually coloring the examination region on an image of the examination data set. This facilitates identification of a particular examination region and thus a subsequent image evaluation, and furthermore saves time.

At least one embodiment of the inventive idea is thus a comparison of an examination data set with a previously stored or determined reference data set containing at least one reference region. Based on the comparison, marking finally takes place of at least one examination region which corresponds to the reference region in terms for example of position, orientation and/or size.

In an advantageous embodiment, the assignment of the reference data set to the read-in examination data set takes place based on information about the examination object. However, this information does not solely comprise e.g. sex, age or an etiopathology of the examination object. Such information may for example also originate from DICOM (Digital Imaging and Communications in Medicine) attributes, i.e. attributes of an open standard for storing and exchanging information in medical image data management. DICOM attributes comprise for instance properties of a contrast or an orientation, or other attributes such as times of a measurement, information about administration of contrast agent or the sex of an examination object. Different attributes can be distinguished in different stages of scalability; for example, they can be scalable nominally, ordinally or cardinally. Because the DICOM standard is widely used, a high degree of compatibility exists, since interoperability between systems of different manufacturers is possible. The assignment based on this information furthermore permits an optimized selection of a reference data set, i.e. a suitable selection of a standard patient consistent with the examination object.

In another embodiment, the assignment of the reference data set to the read-in examination data set comprises a registration of the reference data set with the read-in examination data set. Registration here means a process which brings the reference data set and the read-in examination data set into correlation with one another, for example in respect of an angle of view, a time or a recording position. The registration itself can be applied globally, i.e. predominantly to the complete data sets, or else locally, i.e. predominantly to particular regions of the data sets. The registration preferably takes place automatically, but it can also be initiated manually by a user. This facilitates a subsequent image evaluation, since an at least partial alignment of the image data is already undertaken and moreover saves time.

In a preferred embodiment, the marking of the at least one examination region includes a marking tolerance. Marking tolerance here means a marking which is additional to an original marking, which causes the region marked overall to be larger in comparison to a marking without marking tolerance. In the case of circular marking which is implemented using a circle, this marking tolerance can be implemented using a second circle with the same center point and a larger radius, but the marking tolerance can also represent any possible shape of marking which in range extends beyond the original marking. This enlargement of the marking region increases the probability that e.g. an assumed organ on which the examination region is based is actually located within the marking and the marking tolerance.

In an inventive embodiment, the marking of the at least one examination region comprises a segmentation of the at least one examination region in at least one image of the examination data set. Segmentation here means generation of regions having coherent content by combining adjacent image information, for example pixels or voxels, corresponding to a particular homogeneity criterion. The segmentation can here take place automatically, but at least one suggestion for a segmentation can initially be generated, which has to be confirmed by a user. Based on the suggested segmentation, a suggestion for contouring can moreover be generated, i.e. for an envelope embracing the contiguous region. This once again facilitates identification of a particular examination region and thus a subsequent image evaluation, and furthermore saves time.

In an advantageous embodiment, the segmentation depends on the reference region selected, i.e. the segmentation can be limited to the selected reference region. This corresponds to an optimization, in particular a restriction, of a so-called search area. Search area here means the area which is explored by a segmentation rule for the underlying segmentation. The restricted search area can therefore for example easily be explored for the assumed organs within the examination region. This saves both time and resources.

In another embodiment, the segmentation depends on the medical imaging device. This means that a segmentation rule specifically developed for the medical imaging device used for the examination can be employed. The results of the segmentation, in particular as regards the accuracy of the segmentation, are optimized in this way.

In a preferred embodiment, the reference data set comprises a database, in particular a rule database. A rule database here means a database which contains information about the reference data set, i.e. about the standard patient consistent with the examination object. This information comprises for example information about at least one position of at least one organ relative to at least one anatomical landmark. Based on this information an examination region of the examination data set can once again be inferred from the reference data set. The reference regions are then to be understood as calculation rules for obtaining the examination regions, i.e. the examination regions are obtained using the rules laid down in the database. The anatomical landmarks per se can however also be determined automatically, by automatically identifying significant image regions. This alternative embodiment also facilitates identification of a particular examination region and thus a subsequent image evaluation, and furthermore saves time.

In connection with an embodiment of the present invention an evaluation unit for evaluating an examination of an examination object using a medical imaging device is also provided.

The evaluation unit of an embodiment comprises a processing unit and is configured to perform at least the following:

Reading in an examination data set of the examination object by means of the processing unit, Assigning a reference data set to the read-in examination data set by means of the processing unit, the reference data set comprising at least one reference region, Selecting at least one reference region by means of the processing unit, Assigning at least one examination region of the examination data set to the at least one reference region by means of the processing unit and Marking the at least one examination region in at least one image of the examination data set by means of the processing unit.

Furthermore, a medical evaluation system, comprising an evaluation unit and at least one medical imaging device, is provided for evaluating an examination of an examination object.

Further, an embodiment of the present invention describes a computer program which can be loaded in a memory unit of a programmable controller or a computing unit of an evaluation unit and/or of a medical evaluation system. With this computer program, all or various previously described embodiments of the inventive method can be executed, if the computer program runs in the controller or control facility of the evaluation unit and/or of the medical evaluation system. In such cases the computer program requires possible program means, e.g. libraries and auxiliary functions, in order to realize the corresponding embodiments of the method. In other words, software with which one of the above-described embodiments of the inventive method can be executed or which executes this embodiment is in particular to be protected with the claim focusing on the computer program. In such cases, the software may be a source code, which must still be compiled and bound or which only has to be interpreted, or an executable software code, which is to be loaded for execution purposes into the corresponding computing unit.

Furthermore, an embodiment of the present invention relates to an electronically readable storage medium, e.g. a DVD, a magnetic tape or a USB stick, on which electronically readable control information, in particular software, is stored. If this control information is read from the storage medium and stored in a controller or computing unit of an evaluation unit and/or of a medical evaluation system, all inventive embodiments of the previously described method can be implemented.

The advantages of an embodiment of the inventive evaluation unit, of the inventive medical evaluation system, of the inventive computer program and of the inventive electronically readable storage medium correspond substantially to the advantages of the inventive method, which are explained in detail above. Features, advantages or alternative embodiments mentioned here are likewise also to be transferred to the other claimed subject matters and vice versa. In other words, the objective claims, which focus on an evaluation unit for instance, can also be developed with the features which are described or claimed in conjunction with a method. The corresponding functional features of the method are embodied here by corresponding objective modules, in particular by hardware modules.

FIG. 1 shows an embodiment of an inventive medical evaluation system 103. The medical evaluation system 103 comprises an evaluation unit 101 and a medical imaging device 102, and is designed to evaluate an examination of an examination object.

The medical imaging device 102 is here embodied as a magnetic resonance device. Alternatively, the medical imaging device 102 can also be a combined magnetic resonance/positron emission tomography device or other medical imaging devices 102 which appear expedient to the person skilled in the art.

Figure 2:
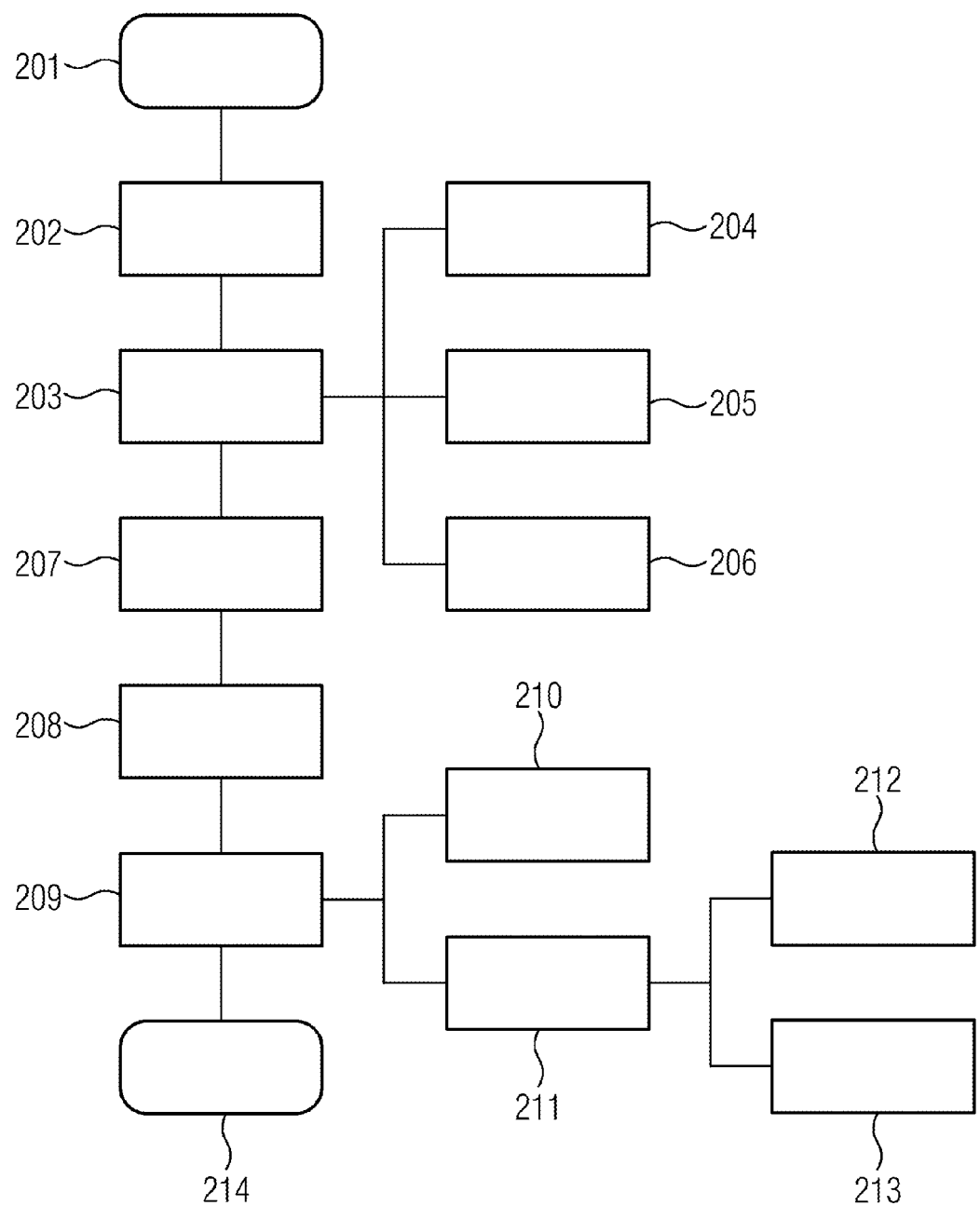
FIG. 2 shows a flow chart of an embodiment of an inventive method.
Figure 3:
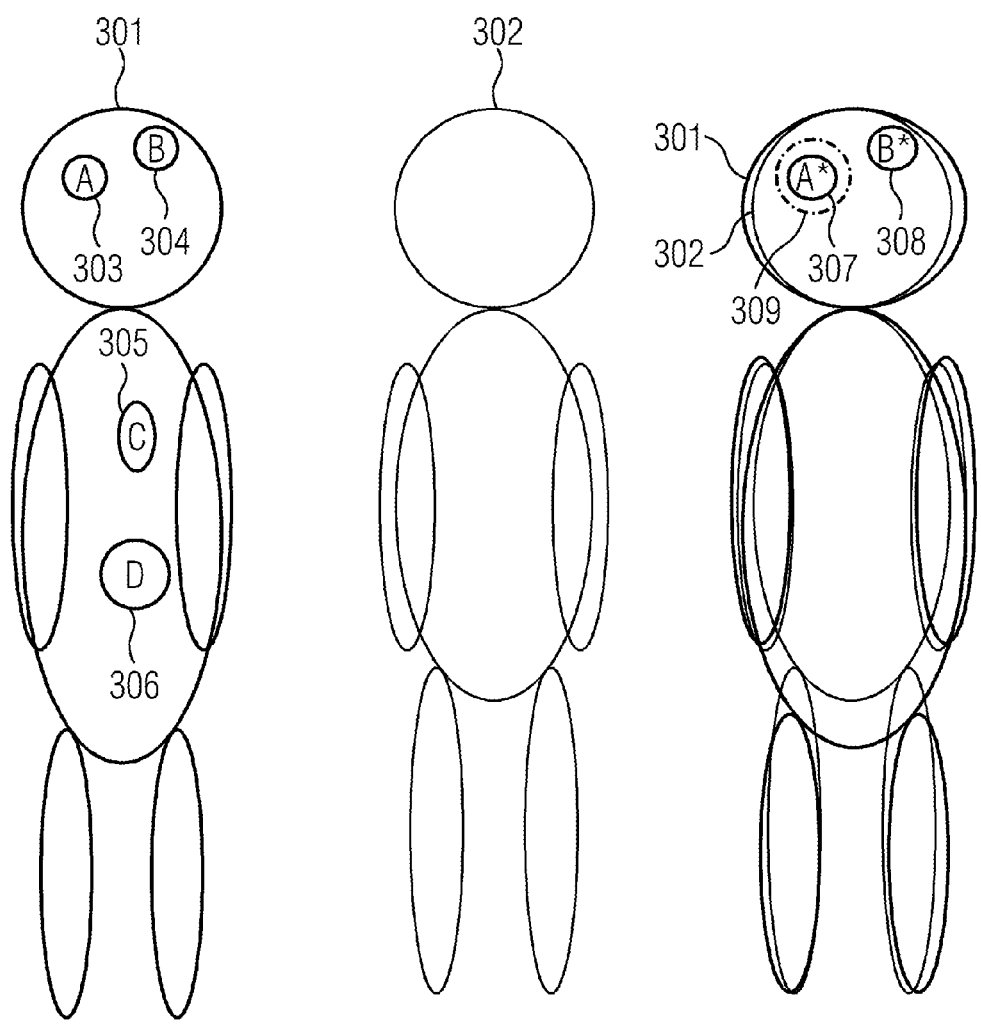
FIG. 3 shows an example of a marking of an examination region based on a reference region.

FIG. 2 shows a flow chart of an embodiment of an inventive method. The method comprises the method steps 201 to 214, wherein, when describing the method steps 201 to 214, description parts including the corresponding reference characters introduced in conjunction with FIGS. 1 and 3 are also used.

The method steps 201 to 212 are here performed by the evaluation unit 101 of the medical evaluation system 103.

A first method step 201 characterizes the start of an evaluation of an examination of an examination object using the medical imaging device 102 via the evaluation unit 101.

In method step 202, an examination data set 302 is read in, here a magnetic resonance data set of the examination object. Reading in comprises reading in at least one image of the examination object. When reading in more than one image it is also possible for the images to originate from different modalities, in other words different medical imaging devices 102.

During a method step 203 a reference data set 301 is assigned to the read-in examination data set 302, the reference data set 301 comprising at least one reference region 303, 304, 305, 306, as illustrated in FIG. 3 for example on the basis of four reference regions 303, 304, 305, 306. The assignment comprises assigning data from a so-called standard patient to the examination object. In this case the standard patient is generally not the current examination object to be examined. The reference data set of the standard patient further comprises the at least one reference region 303, 304, 305, 306, i.e. a particularly outstanding examination region which is advantageous for the evaluation of the examination. In this case a position of the reference region 303, 304, 305, 306, in particular a location and an extent of the reference region 303, 304, 305, 306 within the standard patient, is to be regarded as known.

In method step 204, the reference data set 301 is assigned to the read-in examination data set 302 on the basis of information about the examination object. However, this information does not solely comprise e.g. sex, age or an etiopathology of the examination object. Such information may for example also originate from DICOM (Digital Imaging and Communications in Medicine) attributes, i.e. attributes of an open standard for storing and exchanging information in medical image data management. DICOM attributes comprise for instance properties of a contrast or an orientation, or other attributes such as times of a measurement, information about administration of contrast agent or the sex of an examination object. Different attributes can be distinguished in different stages of scalability, for example they can be scalable nominally, ordinally or cardinally.

In method step 205, the assignment of the reference data set 301 to the read-in examination data set 302 comprises a registration of the reference data set 301 with the read-in examination data set 302. The registration itself can be applied globally, i.e. predominantly to the complete data sets, or else locally, i.e. predominantly to particular regions of the data sets. The registration preferably takes place automatically, but it can also be initiated manually by a user.

In method step 206, the reference data set 301 comprises a database, in particular a rule database. A rule database here means a database which contains information about the reference data set 301, i.e. about the standard patient consistent with the examination object. This information comprises for example information about at least one position of at least one organ relative to at least one anatomical landmark. Based on this information an examination region 307, 308 of the examination data set 302 can once again be inferred from the reference data set 301. The reference regions 303, 304, 305, 306 are then to be understood as calculation rules for obtaining the examination regions 307, 308. The anatomical landmarks per se can however also be determined automatically, by automatically identifying significant image regions.

In the performance of an embodiment of the inventive method, the method steps 204 to 206 can be used as alternatives or can be combined with one another as desired.

During a method step 207, at least one reference region 303, 304, 305, 306 is selected. The selection for example takes place manually by a user or else by a manual or automatic selection of one or more reference regions 303, 304, 305, 306 from a predefined list of reference regions 303, 304, 305, 306. Criteria for such a selection may take account of a region specifically to be examined of the examination object or of other parameters.

In method step 208, at least one examination region 307, 308 of the examination data set 302 is assigned to the at least one reference region 303, 304, 305, 306, while a method step 209 characterizes a marking of the at least one examination region 307, 308 in at least one image of the examination data set 302. In this case, marking for example means selecting a data matrix from the examination data set 302 or else visually coloring the examination region 307, 308 on an image of the examination data set 302.

During a method step 210, the marking of the at least one examination region 307, 308 includes a marking tolerance 309, i.e. a marking which is additional to an original marking, which causes the region marked overall to be larger in comparison to a marking without marking tolerance. The original marking is represented in FIG. 3 by the examination region 307, and the marking tolerance 309 by a circular ring. The marking tolerance can however also represent any possible shape of marking which in range extends beyond the original marking.

In method step 211, the marking of the at least one examination region 307, 308 of the examination data set 302 comprises a segmentation of the at least one examination region 307, 308 in at least one image of the examination data set 302. The segmentation can here take place automatically, but at least one suggestion for a segmentation can initially be generated, which has to be confirmed by a user by means of an input unit of the evaluation unit 101. Based on the suggested segmentation, a suggestion for contouring can moreover be generated, i.e. for an envelope embracing the region to be segmented.

In the performance of an embodiment of the inventive method, the method steps 210 to 211 can be used as alternatives or can be combined with one another as desired.

In method step 212, the segmentation depends on the selected reference region 303, 304, 305, 306, i.e. the segmentation is limited to the selected reference region 303, 304, 305, 306. This corresponds to a restriction of a so-called search area. Search area here means the area which is explored by a segmentation rule for the underlying segmentation. The restricted examination region can therefore for example easily be explored for the assumed organs within the examination region. In method step 213 the segmentation depends on the medical imaging device 102. This means that a segmentation rule specifically developed for the medical imaging device 102 used for the examination can be employed.

A last method step 214 characterizes the end of the evaluation of an examination of an examination object with a medical imaging device 102 by way of an evaluation unit 101.

FIG. 3 shows an example of a marking of an examination region 307, 308 based on a reference region 303, 304, 305, 306.

Initially in method step 202, an examination data set 302 of an examination object is read in. The examination data set 302 is here illustrated in the form of a mapping of an examination object. The reading in takes place by means of an evaluation unit 101.

In a next step, method step 203, a reference data set 301 is assigned to the read-in examination data set 302, the reference data set 301 comprising four reference regions 303, 304, 305, 306, two of which are selected in method step 207. The reference data set is here illustrated in the form of a mapping of a standard patient. The standard patient comprises information from a plurality of patients who are similar to the examination object in a predefined manner. The similarity to the examination object may be established for example by age, sex, size, preexisting or underling diseases or other features defined by a medical specialist. The standard patient may for example be represented by an average image of this plurality of patients.

Now in method step 208, at least one examination region 307, 308 of the examination data set 302 can be assigned based on the four reference regions 303, 304, 305, 306 of the reference data set 301 and then marked as in method step 209. In the example in the figure, two examination regions 307, 308 are assigned and marked, since only one head of the examination object is to be considered.

This assignment and marking is illustrated in FIG. 3 in two different ways.

The assignment can be implemented directly by transferring the reference regions 303, 304 to the associated examination regions 307, 308, by overlaying the mappings of examination object and standard patient and determining the positions of the examination regions 307, 308 in accordance with the positions of the reference regions 303, 304.

The assignment can however for example also take place using a marking tolerance 309. The marking tolerance 309 is here implemented by way of example by an additional circular marking, but the marking tolerance 309 can also represent any possible shape of marking which in range extends beyond the original marking. This causes the region marked overall to be larger in comparison to a marking without marking tolerance 309 and increases the probability that e.g. an assumed organ on which the examination region 307 is based is actually located within the marking and the marking tolerance 309.

Although the invention has been illustrated and described in greater detail on the basis of the preferred exemplary embodiments, the invention is not limited by the disclosed examples and other variations can be derived herefrom by the person skilled in the art without departing from the scope of protection of the invention.

To sum up, an embodiment of the invention relates to a method for evaluating an examination of an examination object using a medical imaging device by way of an evaluation unit, comprising:

Reading in an examination data set of the examination object,

Assigning a reference data set to the read-in examination data set, the reference data set comprising at least one reference region, Selecting at least one reference region, Assigning at least one examination region of the examination data set to the at least one reference region and Marking the at least one examination region in at least one image of the examination data set.

In an advantageous embodiment the marking of the at least one examination region includes a marking tolerance and a segmentation of the at least one examination region on at least one image of the examination data set, and the segmentation depends on the medical imaging device.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for evaluating an examination of an examination object using a medical imaging device, the method comprising:
    reading in an examination data set of the examination object;
    registering a reference data set to the read-in examination data set, the reference data set being a standard patient data corresponding to the examination object, the reference data set including at least one reference region;
    selecting at least one reference region of the reference data set;
    assigning at least one examination region of the examination data set to one of the selected at least one reference region; and
    marking the assigned at least one examination region in at least one image of the examination data set by,
        segmenting the assigned at least one examination region in the at least one image of the examination data set based on the at least one assigned reference region and a corresponding marking tolerance, the corresponding marking tolerance defining an area larger than the corresponding assigned reference region used by a segmentation rule for segmenting the assigned at least one examination region.

2. The method of claim 1, wherein the segmenting is based on the medical imaging device.

3. The method of claim 1, wherein the reference data set comprises a database.

4. The method of claim 1, wherein the segmenting is based on the medical imaging device.

5. The method of claim 1, wherein the area defined by the marking tolerance has a circular shape corresponding to a circular shape of the assigned reference region.

6. A non-transitory computer readable medium comprising computer-readable instructions, which when executed by a processor, causes the processor to perform the method of claim 1.

7. An apparatus configured to evaluate an examination of an examination object using a medical imaging device, the apparatus being configured to,
    read in an examination data set of the examination object;
    register a reference data set to the read-in examination data set, the reference data set being a standard patient data corresponding to the examination object, the reference data set including at least one reference region;
    select at least one reference region of the reference data set;
    assign at least one examination region of the examination data set to one of the selected at least one reference region; and
    mark the assigned at least one examination region in at least one image of the examination data set by,
        segmenting the assigned at least one examination region in the at least one image of the examination data set based on the at least one assigned reference region and a corresponding marking tolerance, the corresponding marking tolerance defining an area larger than the corresponding assigned reference region used by a segmentation rule for segmenting the assigned at least one examination region.

8. A medical evaluation system, comprising:
    the apparatus of claim 7; and
    at least one medical imaging device configured to examine the examination object.

9. The apparatus of claim 7, wherein the area defined by the marking tolerance has a circular shape corresponding to a circular shape of the assigned reference region.

* * * * *